United States Patent [19]

Kita et al.

[11] Patent Number: 5,045,233
[45] Date of Patent: Sep. 3, 1991

[54] METHOD FOR INHIBITING POLYMERIZATION OF MALEIMIDES

[75] Inventors: Yuichi Kita, Akashi; Kentaro Sakamoto, Hyogo; Masao Baba; Tomoaki Tobo, both of Himeji, all of Japan

[73] Assignee: Nippon Shokubai Kagaku Kogyo Co., Ltd., Osaka, Japan

[21] Appl. No.: 114,704

[22] Filed: Oct. 30, 1987

Related U.S. Application Data

[63] Continuation-in-part of Ser. No. 942,182, Dec. 16, 1986, abandoned.

[30] Foreign Application Priority Data

Dec. 19, 1985 [JP] Japan ................................ 60-284209
Dec. 19, 1985 [JP] Japan ................................ 60-284210

[51] Int. Cl.$^5$ ...................... C09K 15/04; C09K 15/10; C09K 15/16
[52] U.S. Cl. .................................. 252/399; 252/402; 252/404; 252/405; 252/406; 252/407; 252/401
[58] Field of Search ................ 526/262; 252/406, 407, 252/399, 401, 402, 404, 405

[56] References Cited

U.S. PATENT DOCUMENTS

| 3,696,050 | 10/1972 | Werts, III et al. | 252/403 |
| 3,781,235 | 12/1973 | Trott . | |
| 4,004,959 | 1/1977 | Ledru . | |
| 4,321,191 | 3/1982 | Minagawa et al. | 524/285 |
| 4,466,905 | 8/1984 | Butler et al. | 252/403 |
| 4,582,883 | 4/1986 | de Koning et al. | 526/262 |
| 4,623,734 | 11/1986 | Kito et al. | 548/545 |

FOREIGN PATENT DOCUMENTS 644144 7/1984 Switzerland .
1041027 10/1963 United Kingdom .
1041027 9/1966 United Kingdom .

OTHER PUBLICATIONS

Plastic Additive Handbook, Gächter & Müller, Macmillan Pub. Co., 1985, pp. 8–13.
Encyclopedia of Pol. Science & Tech., vol. 7, Ed. H. Mark, 1967, pp. 647–649.
Chemical Abstracts, vol. 67, No. 4, Jul. 24, 1967, p. 1140, Abstract No. 11806b, Columbus, Ohio.

Primary Examiner—Peter F. Kulkosky
Attorney, Agent, or Firm—Omri M. Behr

[57] ABSTRACT

A method for inhibiting polymerization of a maleimide, which comprises adding to said maleimide, as a polymerization inhibitor, at least one compound selected from the group consisting of thiodipropionic esters, 4-t-butyl-catechol, 2,4-dimethyl-6-t-butyl phenol, 2,5-di-t-butylhydroquinone, 2-t-butyl-hydroquinone, 2,4-bis-(n-octylthio)-6-(4-hydroxy-3,5-di-t-butylanilino)-1,3,5-trizaine, 2,2'-thiobis-(4-methyl-6-t-butylphenol), 4,4'-thiobis-(6-butyl-m-cresol), and triethyleneglycolbis-[3-(3-t-butyl-5-methyl-4-hydroxyphenyl)propionate].

9 Claims, No Drawings

METHOD FOR INHIBITING POLYMERIZATION OF MALEIMIDES

This is a continuation-in-part of copending application Ser. No. 942,182, filed Dec. 16, 1986, which is now abandoned.

BACKGROUND OF THE INVENTION

1. Field of the Invention

This invention relates to a method for inhibiting polymerization of maleimides. More particularly, it relates to a method for inhibiting polymerization of maleimides by using as a polymerization inhibitor at least one compound selected from the group consisting of thiodipropionic esters, 4-t-butyl-catechol, 2,4-dimethyl-6-t-butyl phenol, 2,5-di-t-butyl-hydroquinone, 2-t-butyl-hydroquinone, 2,4-bis-(n-octylthio)-6-(4-hydroxy-3,5-di-t-butylanilino)-1,3,5-triazine, 2,2'-thiobis-(4-methyl-6-t-butylphenol), 4,4'-thiobis-(6-t-butyl-m-cresol), and triethyleneglycol-bis-[3-(3-t-butyl-5-methyl-4-hydroxyphenyl)propionate]. It provides a method for conspicuously inhibiting polymerization of maleimides by the use of this specific polymerization inhibitor as during the production of maleimides from maleic anhydride and amines, during the purification of crude maleimides as by distillation, for example, or during the storage or transportation of maleimides, for example.

2. Description of the Prior Art

Maleimides, because of their molecular structures, are extremely unstable compounds which readily undergo polymerization. For this reason, various methods have been heretofore proposed for inhibiting polymerization of maleimides as during the production of maleimides from maleic anhydride and amines or during the purification of crude maleimides by distillation, for example. For the purpose of inhibiting polymerization of maleimides during the production or reaction of maleimides, for example, a method which causes a maleimide produced by the heat treatment of maleinamic acid under a vacuum to be quickly expelled by distillation from the reaction system is disclosed in the Japanese Patent Laid-Open No. SHO 47(1972)-27,974. In the Japanese Patent Laid-Open No. SHO 53(1978)-137,956, there is disclosed a method which produces a maleimide by preparatorily adding a hydrogen halide to the double bond of maleic anhydride as a raw material thereby depriving the double bond of polymerization reactivity and then allowing the maleic anhydride to react with an amine thereby effecting ring closing by dehydration. Neither of these patent publications teaches a method for inhibiting polymerization of maleimides and therefore permitting production of maleimides in satisfactorily high yields.

Further, methods which effect purification of crude maleimides while keeping the crude meleimides from exposure to heat as much as possible have been disclosed. In the Japanese Patent Laid-Open Nos. SHO 58(1983)-96,066 and SHO 60(1985)-100,554, for example, there are disclosed methods which effect the purification by recrystallizing the crude maleimides from such solvents as methanol, toluene, or isopropanol at relatively low temperatures.

Even when maleimides are purified under such conditions as described above, polymerization proceeds on the maleimides while the maleimides are held in storage. As the result, the maleimides will be deprived of their commercial value during the course of their storage.

In the case of a maleimide which contains therein the homopolymer of the maleimide, for example, when this maleimide is copolymerized with styrene or with styrene and acrylonitrile, the produced copolymer inevitably contains therein the homopolymer of the maleimide and, therefore, fails to acquire as high improved thermal stability and strength as expected. Further because the homopolymer of maleimide is insoluble in the comonomer, the copolymer is seriously impaired in appearance and transparency in particular and suffers from a heavy decline of commercial value.

It has been known to the art add (2,6-di-tert -butyl p-cresol) as a polymerization inhibitor to maleimides (British Patent No. 1,041,027). This compound has a disadvantage that while it manifests its effect sufficiently at low temperatures, it fails to manifest the effect sufficiently when it is heated to a high temperature.

As described above, it is very important to inhibit polymerization of maleimides as during the courses of production, purification, storage, and transportation. In spite of this importance, virtually no method has yet been proposed for effective inhibition of the polymerization of maleimides.

An object of this invention, therefore, is to provide a method for inhibiting polymerization of maleimides.

Another object of this invention is to provide a method for effectively inhibiting polymerization of maleimides without coloring maleimides.

Yet another object of this invention is to provide maleimide compositions which are prevented from coloration and polymerization.

SUMMARY OF THE INVENTION

The objects described above are accomplished by a method for inhibiting polymerization of maleimides, which comprises adding to the maleimides, as a polymerization inhibitor at least one compound selected from the group consisting of thiodipropionic esters, 4-t-butyl-catechol, 2,4-dimethyl-6-t-butyl phenol, 2,5-di-t-butyl-hydroquinone, 2-t-butyl hydroquinone, 2,4-bis-(n-octylthio)-6-(4-hydroxy-3,5-di-t-butylanilino)-1,3,5-triazine, 2,2'-thiobis-(4methyl-6-t-butylphenol), 4,4'-thiobis-(6-t-butyl-m-cresol), and triethyleneglycol-bis-[3-(3-t-butyl-5-methyl-4-hydroxyphenyl)propionate].

These objects are accomplished by a polymerization inhibited maleimide composition, which comprises a maleimide and at least one compound selected from the group consisting of thiodipropionic ester, 4-t-butyl catechol, 2,4-dimethyl-6-t-butyl phenol, 2,5-di-t-butyl-hydroquinone, 2-t-butyl-hydro-quinone, 2,4-bis-(n-octylthio)-6-(4-hydroxy-3,5-di-t-butylaniline)-1,3,5-triazine, 2,2'-thiobis-(4-methyl-6-t-butylphenol), 4,4'-thiobis-(6-t-butyl-m-cresol), and triethyleneglycol-bis[3-(3-t-butyl-5-methyl-4-hydroxyphenyl)propionate].

DESCRIPTION OF PREFERRED EMBODIMENT

This invention is directed to efficiently inhibiting polymerization of a maleimide without coloration of the maleimide, by the addition to the maleimide at least one compound selected from the group consisting of thiodipropionic esters, 4-t-butyl-catechol, 2,4-dimethyl-6-t-butyl phenol, 2,5-di-t-butyl-hydroquinone, 2-t-butyl-hydroquinone, 2,4-bis-(n-octylthio)-6-(4-hydroxy-3,5-di-t-butylanilino)1,3,5-triazine, 2,2'-thiobis-(4-methyl-6-t-butylphenol), 4,4'thiobis-(6-t-butyl-m-cresol), and triethyleneglycol-bis[3(3-t-butyl-5-methyl-4-hydroxyphenyl)-propionate].

As examples of the aforementioned thiodipropionic esters, there can be cited ditridecyl-3,3'-thiodipropionate, dilauryl-3,3'-thiodipropionate, ditetradecyl-3,3'-thiodipropionate, distearyl-3,3'-thiodipropionate, and dioctyl-3,3'-thiodipropionate.

As compared with p-methoxyphenol and hydroquinone which have been heretofore used as polymerization inhibitors, the thiodipropionic esters specified by this invention bring about clearly different effects in inhibiting polymerization of maleimides as demonstrated afterward in working examples and comparative experiments.

The maleimides to which the method for inhibition of polymerization contemplated by this invention can be effectively applied are the compounds represented by the general formula I:

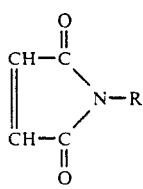

wherein R stands for one member selected from the class consisting of hydrogen atom, an alkyl group of 1 to 20 carbon atoms, phenyl group, benzyl group, cyclohexyl group, pyridyl group, quinolyl group, and the groups mentioned above severally having a halogen substitution, a carboxyl group substitution, or nitro group substitution, preferably alkyl groups or phenyl group. Typical example of these compounds include maleimide, N-methyl maleimide, N-ethyl maleimide, N-hexyl maleimide, N-octyl maleimide, N-dodecyl maleimide, N-benzyl maleimide, N-cyclohexyl maleimide, N-phenyl maleimide, N-nitrophenyl maleimide, N-methoxyphenyl maleimide, N-methylphenyl maleimide, N-carboxyphenyl maleimide, N-hydroxyphenyl maleimide, N-chlorophenyl maleimide, N-dimethylphenyl maleimide, N-dichlorophenyl maleimide, N-bromophenyl maleimide, N-dibromophenyl maleimide, N-trichlorophenyl maleimide, and N-tribromophenyl maleimide. Other examples of the compounds are solutions containing at least one of the maleimides mentioned above, i.e. solutions of such maleimides in acrylonitrile, styrene, maleic anhydride, and (meth)acrylic esters, and mixtures of such solutions. These examples are meant purely for illustration and are not limitative at all.

The aforementioned compound as a polymerization inhibitor can be used for the purpose of bringing about its outstanding effect in the inhibition of polymerization at any step throughout the entire course of production of a maleimide such as, for example, the preparation of raw material, the reaction of amidation, the reaction of imidation, the purification, the storage of produced maleimide, or the transportation of produced maleimide. Particularly when a maleimide is to be preserved for a long time, the polymerization inhibitor enables the maleimide to be stably preserved without inducing change of hue.

Although the amount of the compound (polymerization inhibitor) to be used is to be suitably decided in accordance with the temperature, duration, pressure, gaseous-phase composition, and liquid-phase composition prevalent in each of the steps involved, it is generally in the range of 0.0001 to 1 part by weight, desirably 0.001 to 0.1 part by weight. It is permissible to use this compound in combination with any of the other known polymerization inhibitors such as, for example, hydroquinone and p-methoxyphenol. As concerns the manner of addition of this polymerization inhibitor to a maleimide, the polymerization inhibitor may be added directly in the form of liquid or powder or it may be added as dissolved in a solvent or in any of the raw materials being used.

Generally, maleimides are used as agents for improving the thermal stability of ABS resin, AAS resin, AS resin, and ACS resin, in most cases, as copolymerized with such polymerizable monomers as acrylonitrile and styrene. For this purpose, the maleimides can be transported or conveyed in tank lorries or tank cars, stored in storage tanks, and then put to use directly in the relevant reactions. The specific polymerization inhibitor contemplated by this invention manifests a conspicuous effect even in inhibiting polymerization of solutions of such maleimides in acrylonitrile. Generally, maleimides are stimulative on the human system. When they are left adhering to the skin, they cause inflammation. When their fine powders are inhaled, they stimulate nasal cavities and throats. When these maleimides of undesirable qualities are stabilized to resist polymerization by the use of the polymerization inhibitor and then prepared in the form of solutions in acrylonitrile or in the mixture of acrylonitrile with styrene, they can be handled safely in a liquid state. In this case, the amount of acrylonitrile or the mixture of acrylonitrile with styrene to be used in the preparation of the aforementioned maleimide solution is in the range of 10 to 10,000 parts by weight, desirably 50 to 5,000 parts by weight, and most desirably 100 to 1,000 parts, based on 100 parts by weight of maleimides to be dissolved.

Now, the present invention will be described more specifically below with reference to working examples.

Examples 1–31 and Controls 1–8

A various species of maleimide and a various species of polymerization inhibitor were placed in respectively various amounts in a test tube and heated in an oil bath at 150{C. for 3 hours. In this case, the gaseous phase of the sealed test tube was filled with nitrogen gas. After 3 hours' heating, the sealed test tube was removed from the oil bath and the maleimide mixed with the polymerization inhibitor was cooled. The cooled maleimide mixture was pulverized and analyzed for purity by means of highperformance liquid chromatography. The results were as shown in Table 1.

TABLE 1

| Example No. | Species of maleimide | Species of polymerization inhibitor | Amount of P. I.* added (ppm) | Purity before heating (wt %) | Purity after heating (wt %) | Appearance before heating | Appearance after heating |
|---|---|---|---|---|---|---|---|
| 1 | N-phenyl maleimide | Ditridecyl-3,3'-thiodipropionate | 100 | 99.8 | 99.6 | Yellow crystals | Yellow crystals |
| 2 | N-phenyl maleimide | Dilauryl-3,3'-thiodepropionate | " | " | 99.4 | Yellow crystals | Yellow crystals |

TABLE 1-continued

| Example No. | Species of maleimide | Species of polymerization inhibitor | Amount of P.I.* added (ppm) | Purity before heating (wt %) | Purity after heating (wt %) | Appearance before heating | Appearance after heating |
|---|---|---|---|---|---|---|---|
| 3 | N-phenyl maleimide | Distearyl-3,3'-thiodipropionate | " | " | 99.6 | Yellow crystals | Yellow crystals |
| 4 | Maleimide | Distearyl-3,3'-thiodipropionate | " | 99.9 | 99.1 | White crystals | White crystals |
| 5 | N-methyl maleimide | Distearyl-3,3'-thiodipropionate | " | 99.8 | 99.3 | White crystals | White crystals |
| 6 | N-dodecyl maleimide | Distearyl-3,3'-thiodipropionate | " | 98.7 | 98.2 | White crystals | White crystals |
| 7 | N-cyclohexyl maleimide | Distearyl-3,3'-thiodipropionate | " | 99.5 | 99.1 | White crystals | White crystals |
| 8 | N-o-chlorophenyl maleimide | Distearyl-3,3'-thiodipropionate | " | 98.9 | 98.6 | Light yellow crystals | Light yellow crystals |
| 9 | N-o-methylphenyl maleimide | Distearyl-3,3'-thiodipropionate | " | 99.5 | 99.0 | Light yellow crystals | Light yellow crystals |
| 10 | N-phenyl maleimide | Distearyl-3,3'-thiodipropionate | 10 | 99.8 | 99.1 | Yellow crystals | Yellow crystals |
| 11 | N-phenyl maleimide | Distearyl-3,3'-thiodipropionate | 1000 | " | 99.6 | Yellow crystals | Yellow crystals |
| 12 | N-phenyl maleimide | Distearyl-3,3'-thiodipropionate | 10000 | " | " | Yellow crystals | Yellow crystals |
| 13 | N-phenyl maleimide | Ditetradecryl-3,3'-thiodipropionate | 100 | 99.8 | 99.6 | Yellow crystals | Yellow crystals |
| 14 | N-phenyl maleimide | Dioctyl-3,3'-thiodepropionate | " | " | " | Yellow crystals | Yellow crystals |
| 15 | N-phenyl maleimide | 4-tert-Butyl catechol | " | " | 99.7 | Yellow crystals | Yellow crystals |
| 16 | N-phenyl maleimide | 2,4-Dimethyl-6-t-butyl phenol | " | " | 99.6 | Yellow crystals | Yellow crystals |
| 17 | Maleimide | 4-tert-Butyl-catechol | " | 99.9 | 99.2 | White crystals | White crystals |
| 18 | N-methyl maleimide | 4-tert-Butyl-catechol | " | 99.8 | 99.4 | White crystals | White crystals |
| 19 | N-dodecyl maleimide | 4-tert-Butyl-catechol | " | 98.7 | 98.4 | White crystals | White crystals |
| 20 | N-cyclohexyl maleimide | 4-tert-Butyl-catechol | " | 99.5 | 99.3 | White crystals | White crystals |
| 21 | N-o-chlorophenyl maleimide | 4-tert-Butyl-catechol | " | 98.9 | 98.6 | Light yellow crystals | Light yellow crystals |
| 22 | N-o-methylphenyl maleimide | 4-tert-Butyl-catechol | " | 99.5 | 99.2 | Light yellow crystals | Light yellow crystals |
| 23 | N-phenyl maleimide | 4-tert-Butyl-catechol | 10 | 99.8 | 99.1 | Yellow crystals | Yellow crystals |
| 24 | N-phenyl maleimide | 4-tert-Butyl-catechol | 1000 | " | 99.7 | Yellow crystals | Yellow crystals |
| 25 | N-phenyl maleimide | 4-tert-Butyl-catechol | 10000 | " | " | Yellow crystals | Yellow crystals |
| 26 | N-phenyl maleimide | 2,5-Di-tert-butyl-hydroquinone | 100 | 99.8 | 99.4 | Yellow crystals | Yellow crystals |
| 27 | N-phenyl maleimide | 2-tert-Butyl hydroquinone | " | " | 99.5 | Yellow crystals | Yellow crystals |
| 28 | N-phenyl maleimide | 4,4'-Thiobis-(6-tert-butyl-m-cresol) | " | " | 99.4 | Yellow crystals | Yellow crystals |
| 29 | N-phenyl maleimide | 2,2'-Thiobis(4-methyl-6-tert-butylphenol) | " | " | 99.6 | Yellow crystals | Yellow crystals |
| 30 | N-phenyl maleimide | TGBP | " | " | 99.6 | Yellow crystals | Yellow crystals |
| 31 | N-phenyl maleimide | BOHT | " | " | 99.5 | Yellow crystals | Yellow crystals |
| C.1 | N-phenyl maleimide | None | 0 | 99.8 | 60.5 | Yellow crystals | Orange resin |
| C.2 | N-phenyl maleimide | Hydroquinone | 100 | " | 90.2 | Yellow crystals | Brown crystals |
| C.3 | N-phenyl maleimide | p-Methoxyphenol | " | " | 90.8 | Yellow crystals | Brown crystals |
| C.4 | N-phenyl maleimide | Phenothiazine | " | " | 93.5 | Yellow crystals | Reddish brown crystals |
| C.5 | N-phenyl maleimide | Thiourea | " | " | 87.3 | | Brown crystals |
| C.6 | N-phenyl maleimide | Thioglycolic acid | " | " | 90.2 | Yellow crystals | Brown crystals |
| C.7 | N-phenyl maleimide | Copper dimethyl-dithiocarbamate | " | " | 95.2 | Yellow crystals | Brown crystals |
| C.8 | N-phenyl maleimide | 2,6-Di-tert-butyl- | 100 | 99.8 | 95.3 | Yellow | Yellow |

TABLE 1-continued

| Example No. | Species of maleimide | Species of polymerization inhibitor | Amount of P. I.* added (ppm) | Purity before heating (wt %) | Purity after heating (wt %) | Appearance before heating | Appearance after heating |
|---|---|---|---|---|---|---|---|
| | | p-cresol | | | | crystals | crystals |

Note
TGBP = Triethyleneglycol-bis[3-(3-tert-butyl-5-methyl-4-hydroxyphenyl)propionate]
BOHT = 2,4-Bis-(n-octylthio)-6-(4-hydroxy-3,5-di-tert-butylanilino)-1,3,5-triazine

Example 32

In a stainless steel container provided with a heating jacket and measuring 10 cm in diameter and 20 cm in height, 1 kg of yellow N-phenyl maleimide having a purity of 99.8% by weight and 0.2 g of 4-tert-butyl catechol were heated at an inner temperature of 100° C., with heat applied from the jacket. At this time, N-phenyl maleimide was a yellow liquid. The gaseous phase inside the container was filled with nitrogen gas.

The container and the contents thereof were left standing in the condition for 30 days. At the end of the 30 days' standing, the N-phenyl maleimide was found to be retaining the original color. On analysis by high-performance liquid chromatography, this maleimide was found to possess a purity of 99.7 % by weight except for the polymerization inhibitor content, indicating substantial absence of change during the protracted standing.

Example 33

In a stainless steel container provided with a heating jacket and measuring 10 cm in diameter and 20 cm in height, 1 kg of yellow N-phenyl maleimide having a purity of 99.8% by weight and 0.1 g of distearyl-3,3'-thiodipropionate were heated at an inner temperature of 100° C., with heat applied from the jacket. At this time, N-phenyl maleimide was a yellow liquid. The gaseous phase inside the container was filled with nitrogen gas.

The container and the contents thereof were left standing in the condition for 30 days. At the end of the 30 days' standing, the N-phenyl maleimide was found to be retaining the original color. On analysis by high-performance liquid chromatography, this maleimide was found to possess a purity of 99.6% by weight except for the polymerization inhibitor content, indicating substantial absence of change during the protracted standing.

Example 34

A flask having an inner volume of 500 ml and provided with a stirrer and a condenser was charged with 100 g of acrylonitrile and 10 mg of ditridecyl-3,3'-thiodipropionate. Over a water bath, the flask was heated to raise the inner temperature thereof to 30° C. Then, the contents of the flask were kept stirred and 100 g of N-phenyl maleimide crystals having a purity of 99.5% by weight were added to the stirred contents. Consequently, the crystals of N-phenyl maleimide were quickly dissolved to give rise to a perfectly transparent yellow acrylonitrile solution.

Then, the gaseous phase inside the container was filled with nitrogen gas and this solution was left standing at an inner temperature of 50° C. for 30 days. Even after 30 days' standing, the solution retained the transparency intact. When this solution was distilled to expel acrylonitrile, there were obtained bright yellow crystals. These crystals, on analysis by highperformance liquid chromatography, were found to have N-phenyl maleimide content of 99.5% by weight except for the polymerization inhibitor content. Absolutely no part of the maleimide was found to have undrgone polymerization.

Example 35

A prefectly clear yellow acrylonitrile solution was obtained by following the procedure of Example 34, excepting 50 mg of p-tert-butyl catechol was added in the place of 10 mg of ditridecyl-3,3'-thiodipropionate.

Then, the solution was left standing at an inner temperature of 50° C. for 30 days. Even after 30 days' standing, the solution retained the clarity intact. When this solution was distilled to expel acrylonitrile, there were obtained bright yellow crystals. These crystals, on analysis by highperformance liquid chromatography, were found to have N-phenyl maleimide content of 99.5% by weight except for the polymerization inhibitor content. Absolutely no part of the maleimide was found to have undergone polymerization.

Example 36

A clear light yellow acrylonitrile 50% by weight N-(o-methylphenyl)-maleimide solution was obtained by following the procedure of Example 34, excepting N-(o-methylphenyl)maleimide having a purity of 99.5% by weight was used in the place of N-phenyl maleimide and 100 mg of triethyleneglycol-bis [3-(3-tert-butyl-5-methyl-4-hydroxyphenyl) propionate] was used in the place of ditridecyl-3,3'-thiodipropionate.

This solution was left standing at an inner temperature of 50° C. for 30 days. After the 30 days' standing, this solution was distilled to expel acrylonitrile. Consequently, there were obtained bright light yellow crystals. The crystals, on analysis by high-performance liquid chromatography, were found to have N-(o-methylphenyl)maleimide content of 99.5% by weight except for the polymerization inhibitor content, indicating that absolutely no part of the maleimide had undergone polymerization.

Example 37

A clear light yellow acrylonitrile 50% by weight N-(o-chlorophenyl)maleimide solution was obtained by following the procedure of Example 34, excepting N-(o-chlorophenyl)maleimide having a purity of 99.0% by weight was used in the place of N-phenyl maleimide and 30 mg of 2,2'-thiobis-(4-methyl-6-tert-butyl phenol) was used in the place of 10 mg of ditridecyl-3,3'-thiodipropionate.

This solution was left standing at an inner temperature of 50° C. for 30 days. After the 30·days' standing, the solution was distilled to expel acrylonitrile. Consequently, there were obtained bright light yellow crystals. The crystals, on analysis by highperformance liquid chromatography, were found to have N-(o-chlorophenyl)maleimide content of 99.0% by weight except for the polymerization inhibitor content, indicating that absolutely no part of the maleimide had undergone polymerization.

Example 38

A flask having an inner volume of 500 ml and provide with a stirrer and a condenser was charged with 100 g of acrylonitrile, 100 g of styrene, and 100 mg of triethyleneglycol-bis [3-(3-t-butyl-5-methyl-4-hydroxyphenyl)propionate]. This solution was kept heated at an inner temperature of 30° C. The solution was kept stirred and 50 g of N-phenyl maleimided crystals having a purity of 99.5% by weight were added to the stirred solution. The N-phenyl maleimide crystals were quickly dissolved to give rise to a perfectly clear yellow solution.

This solution was left standing at 30° C. for 30 days. Even after 30 days' standing, the solution retained the clarity intact. When this solution was distilled to expel acrylonitrile and styrene, there were obtained bright yellow crystals. The crystals, on analysis by highperformance liquid chromatography, were found to have N-phenyl maleimide content of 99.5% by weight except for the polymerization inhibitor content, indicating that substantially no polymerization had occurred in the maleimide-styreneacrylonitrile ternary system.

Examples 39-40

The procedure of Example 38 was repeated, excepting 100 mg of 2,4-bis-(n-octylthio)-6-(4-hydroxy-3,5-di-t-butylanilino)-1,3,5-triazine (Example 39) and 100 mg of 2,2'-thiobis-(4-methyl-6-t-butylphenol) (Example 40) were respectively used in the place of 100 mg of triethylene glycol-bis[3-(3-t-butyl-5-methyl-4-hydroxyphenyl)propionate]. The two crops of crystals consequently obtained were found to have N-phenyl maleimide content of 99.5% by weight except for the polymerization inhibitor content, indicating that substantially no polymerization had occurred in either of the maleimide-styrene-acrylonitrile ternary systems.

Examples 41-45

Various species of polymerization inhibitor were placed in respectively various amounts in a test tube and heated in an oil bath at 155° C. for 8 hours. In this case, the gaseous phase of the sealed test tube was filled with air. After 8 hours' heating, the sealed test tube was removed from the oil bath and the maleimide mixed with the polymerization inhibitor was cooled. The cooled maleimide mixture was pulverized and analyzed for purity by means of highperformance liquid chromatography. The results were as shown in Table 2.

thiodipropionic esters, 4-t-butyl catechol, 2,4-dimethyl-6-t-butyl phenol, 2,5-di-t-butyl hydroquinone, 2-t-butyl hydroquinone, 2,4-bis-(n-octylthio) 6-(4-hydroxy-3,5-di-t-butylanilino)-1,3,5-triazine, 2,2'-thiobis-(4-methyl-6-t-butylphenol), 4,4'-thiobis-(6-tbutyl-m-cresol), and triethyleneglycol-bis[3-(3-t-butyl-5methyl-4-hydroxyphenyl)propionate].

2. A composition according to claim 1, wherein said polymerization inhibitor is a thiodipropionic ester.

3. A composition according to claim 2, wherein said thiodipropionic ester is at least one member selected from the group consisting of ditridecyl-3,3'-thiodipropionate, dilauryl-3,3'-thiodipropionate, ditetradecyl-3,3'-thiodipropionate, distearyl-3,3'-thiodipropionate, and dioctyl-3,3'-thiodipropionate.

4. A composition according to claim 1, wherein said polymerization inhibitor is at least one member selected from the group consisting of 4-t-butyl-catechol, 2,4-dimethyl-1-6-t-butyl phenol, 2,5-di-t-butyl-hydroquinone, and 4,4'-thiobis-(6-t-butyl-m-cresol).

5. A composition according to claim 1, wherein the amount of said polymerization inhibitor is in the range of 0.0001 to 1 parts by weight based on 100 parts by weight of said maleimide.

6. A composition according to claim 1, wherein said maleimide is a compound represented by the following general formula I:

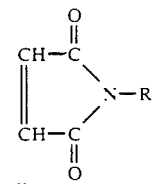

wherein R stands for one member selected from the class consisting of a hydrogen atom, alkyl groups of 1 to 20 carbon atoms, phenyl group, benzyl group, cyclohexyl group, pyridyl group, quinolyl group, and the groups mentioned above severally having a halogen substitution, a carboxyl group substitution, or nitro group substitution, preferably alkyl groups or phenyl group.

7. A composition according to claim 1, wherein said maleimide is in the form of a solution in a mixture of acrylonitrile with styrene.

8. A composition according to claim 1, wherein the amount of acrylonitrile is in the range of 10 to 10,000 parts by weight based on 100 parts by weight of said maleimide.

9. A composition according to claim 7, wherein the

TABLE 2

| Example No. | Species of maleimide | Species of polymerization inhibitor | Amount of P. I. added (ppm) | Purity before heating (wt %) | Purity after heating (wt %) | Appearance before heating | Appearance after heating |
|---|---|---|---|---|---|---|---|
| 41 | N-phenyl maleimide | 4-tert-Butyl catechol | 100 | 99.9 | 99.1 | Yellow crystals | Yellow crystals |
| 42 | N-phenyl maleimide | Distearyl-3,3'-thiodipropionate | 100 | 99.9 | 97.8 | Yellow crystals | Yellow crystals |
| 43 | N-phenyl maleimide | 2,4-Dimethyl-6-tert-butyl phenol | 100 | 99.9 | 98.8 | Yellow crystals | Yellow crystals |
| 44 | N-phenyl maleimide | 2,6-di-tert-butyl-p-cresol | 100 | 99.9 | 87.5 | Yellow crystals | Yellow crystals |
| 45 | N-phenyl maleimide | None | — | 99.9 | 43.2 | Yellow crystals | Orange resin formed |

What is claimed is:

1. A polymerization proof maleimide composition which composition consists essentially of (a) a maleimide (b) acrylonitrile and (c) at least one polymerization inhibitor selected from the group consisting of amount of said mixture of acrylonitrile with styrene is in the range of 10 to 10,000 parts by weight based on 100 parts by weight of said malemide.

* * * * *